United States Patent
Wilhelm et al.

(10) Patent No.: US 6,210,659 B1
(45) Date of Patent: Apr. 3, 2001

(54) AQUEOUS PEARLESCING CONCENTRATES

(75) Inventors: Josef Wilhelm, Huenfeld; Rudolf Bimczok, Seeheim-Jugenheim; Werner Kohl, Huenfeld; Achim Ansmann, Erkrath; Rolf Kawa, Monheim, all of (DE)

(73) Assignees: Henkel Kommanditgesellschaft auf Aktien, Duesseldorf; Wella Aktiengesellschaft Wella AG, Darmstadt (DE)

( * ) Notice: Subject to any disclaimer, the term of this patent is extended or adjusted under 35 U.S.C. 154(b) by 0 days.

(21) Appl. No.: 09/308,085
(22) PCT Filed: Nov. 4, 1997
(86) PCT No.: PCT/EP97/06084
   § 371 Date: May 12, 1999
   § 102(e) Date: May 12, 1999
(87) PCT Pub. No.: WO98/20844
   PCT Pub. Date: May 22, 1998

(30) Foreign Application Priority Data

Nov. 13, 1996 (DE) ............................................. 196 46 882

(51) Int. Cl.⁷ .................................................... A61K 7/075
(52) U.S. Cl. ................. 424/70.24; 424/70.1; 424/70.19; 424/70.21; 424/70.22
(58) Field of Search ............................ 424/70.24, 70.21; 514/784, 777, 785

(56) References Cited

U.S. PATENT DOCUMENTS

| | | | |
|---|---|---|---|
| 4,172,887 | 10/1979 | Vanlerberghe et al. | 424/70 |
| 4,777,038 | 10/1988 | Ingeborg | 424/70 |
| 5,213,792 | 5/1993 | Grundmann et al. | 424/70 |
| 5,374,716 | 12/1994 | Biermann et al. | 536/18.6 |
| 5,540,853 * | 7/1996 | Trinh et al. | 510/101 |
| 5,576,425 | 11/1996 | Hill et al. | 536/18.6 |
| 5,653,970 * | 8/1997 | Vermeer | 424/70.24 |
| 5,670,471 | 9/1997 | Amalric et al. | 510/416 |
| 5,711,899 | 1/1998 | Kawa et al. | 252/311 |

FOREIGN PATENT DOCUMENTS

| | | |
|---|---|---|
| 11 65 574 | 3/1964 | (DE) . |
| 20 24 051 | 12/1971 | (DE) . |
| 35 19 080 | 12/1986 | (DE) . |
| 37 24 547 | 2/1989 | (DE) . |
| 42 24 715 | 2/1994 | (DE) . |
| 195 11 570 | 10/1996 | (DE) . |
| 0 181 773 | 5/1986 | (EP) . |
| 0 285 389 | 10/1988 | (EP) . |
| 0 301 298 | 2/1989 | (EP) . |
| 0 367 939 | 5/1990 | (EP) . |
| 0 376 083 | 7/1990 | (EP) . |
| 0 568 848 | 11/1993 | (EP) . |
| 0 684 302 | 11/1995 | (EP) . |
| 2 252 840 | 6/1975 | (FR) . |
| 962 919 | 7/1964 | (GB) . |
| 1 333 475 | 10/1973 | (GB) . |
| WO90/03977 | 4/1990 | (WO) . |
| WO92/13512 | 8/1992 | (WO) . |
| WO93/15171 | 8/1993 | (WO) . |
| WO93/18737 | 9/1993 | (WO) . |
| WO94/24248 | 10/1994 | (WO) . |
| WO95/03782 | 2/1995 | (WO) . |
| WO95/13863 | 5/1995 | (WO) . |
| WO96/21711 | 7/1996 | (WO) . |
| WO96/30475 | 10/1996 | (WO) . |
| WO96/31586 | 10/1996 | (WO) . |

OTHER PUBLICATIONS

Parfumerie und Kosmetik, vol. 75, (1994) pp. 578–580.
Seifen–Ole–Fette–Wachse, vol.193, (1982) pp.373–376.
Happi, Nov. (1996) pp. 70, 72, 75.
Tenside Detergents, vol. 23, (1986) pp.309–313.
Soap/Cosmetics/Chemical Specialties, vol. 16, (1990) pp. 46,X,50,114,116.
Euro Cosmetics, vol.1 (1994) pp.14–16.
Kosmetische Farbemittel, (1984) pp.81–106.
Derwent Patent Abstract No. 96–455332/45.
Derwent Patent Abstract No. 96–443827/45.
Derwent Patent Abstract No. 93/345868/44.
Derwent Patent Abstract No. 86–326195/50.
Derwent Patent Abstract No. 89–025571/04.
Derwent Patent Abstract No. 90–202002/27.
Derwent Patent Abstract No. 92–277291/34.
Derwent Patent Abstract (WPAT) No. 96–001026/01.
Derwent Patent Abstract No. 95–200222/26.
Derwent Patent Abstract No. 90–148725/20.
Derwent Patent Abstract (WPAT) No. 89–032811/05.
Derwent Patent Abstract No. 90–109072/15.
Derwent Patent Abstract No. 66–01585F/00.
Derwent Patent Abstract No. 71–73611s/46.
Derwent Patent Abstract No. 75–39724W/24.

* cited by examiner

Primary Examiner—Thurman K. Page
Assistant Examiner—P. E. McQueeney
(74) Attorney, Agent, or Firm—John E. Drach; Steven J. Trzaska

(57) ABSTRACT

A pearlescent concentrate containing: (a) from 30 to 80% by weight of an alkyl ether sulfatef; (b) from 5 to 20% by weight of a surfactant selected from the group consisting of a betaine, an alkyl and/or alkenyl oligoglycoside, and mixtures thereof; and (c) from 1 to 10% by weight of an (oligo)ethylene glycol mono- and/or difatty acid ester, all weights being based on the total weight of the composition, and wherein the concentrate is polyol-free.

16 Claims, No Drawings

AQUEOUS PEARLESCING CONCENTRATES

BACKGROUND OF THE INVENTION

This invention relates to aqueous polyol-free pearlescing concentrates based on selected surface-active emulsifiers and pearlescent waxes and to their use for the production of pearlescent surface-active compositions.

For centuries, the softly shimmering luster of pearls has held a particular fascination for human beings. It is therefore no wonder that manufacturers of cosmetic preparations endeavour to give their products an attractive, valuable and rich appearance. The first pearlescence used in cosmetics in the middle ages was a pearlescent paste of natural fish scales. At the beginning of the present century, it was discovered that bismuth oxide chlorides were also capable of producing pearlescence. By contrast, pearlescing waxes, particularly of the glycol monofatty acid ester and difatty acid ester type, are of importance in modem cosmetics, being used mainly for the production of pearlescence in hair shampoos and shower gels. An overview of modem pearlescing formulations was published by A. Ansmann and R. Kawa in Parf. Kosm., 75, 578 (1994).

Large numbers of pearlescing compositions and formulations are known from the prior art. For example, DE-A1 35 19 080 (Henkel) describes free-flowing pearlescing concentrates containing 5 to 15% by weight glycol esters, 1 to 6% by weight fatty acid monoethanolamides and 1 to 5% by weight nonionic ethylene oxide adducts with HLB values of 12 to 18. DE-A1 37 24 547 (Henkel) relates to alkanolamide-free pearlescing concentrates which contain 5 to 20% by weight fatty acids and 3 to 10% by weight emulsifiers in addition to glycol fatty acid esters. According to European patents EP-B1 0 376 083 and EP-B1 0 570 398 (Henkel), 15 to 40% by weight glycol fatty acid esters are processed together with 5 to 55% by weight nonionic ampholytic or zwitterionic emulsifiers and 0.1 to 5% by weight or 15 to 40% by weight glycerol to form a pearlescing concentrate. Free-flowing preservative-free pearlescing dispersions containing surfactants (betaines, anionic surfactants, ethoxylates) and glycerol in addition to glycol fatty acid esters are known from DE-A1 42 24 715 (Hoechst). EP-A1 0 684 302 (Th. Goldschmidt) proposes pearlescers containing polyglycerol esters. European patents EP-B1 0 181 773 and EP-B1 0 285 389 (Procter & Gamble) disclose silicone-containing shampoo formulations which contain long-chain acyl compounds as pearlescing waxes. The use of alkyl polyglucosides and selected other surfactants (alkyl sulfates, fatty acid isethionates, betaines and the like) as emulsifiers for the production of pearlescing compositions is known from WO 93/15171 and WO 95/03782 (ICI) and from WO 94/24248 (Henkel Corp.) and WO 95/13863 (SEPPIC). Finally, pearlescent hair conditioners containing selected cationic surfactants are described in EP-A1 0 367 939 (Wella).

Despite this extensive prior art, the problem of providing aqueous pearlescing concentrates, for example as raw materials for the production of hair shampoos, which flow as superconcentrates, even in the absence of polyols (for example glycerol), still exists. Accordingly, the problem addressed by the present invention was to remedy this deficiency.

DESCRIPTION OF THE INVENTION

The present invention relates to aqueous polyol-free pearlescing concentrates containing (a) alkyl ether sulfates,
(b1) betaines and/or
(b2) alkyl and/or alkenyl oligoglycosides and
(c) (oligo)ethylene glycol mono- and/or difatty acid esters.

It has surprisingly been found that an emulsifier mixture of selected anionic and nonionic or amphoteric surfactants, together with pearlescing waxes, can be used for the production of aqueous pearlescing concentrates which flow in highly concentrated form without requiring the presence of polyols, for example glycerol. The invention includes the observation that components (a) and (b) form liquid crystalline phases.

Alkyl ether sulfates

It is known that alkyl ether sulfates are anionic surfactants which are industrially produced by the sulfation of fatty alcohol polyglycol ethers with $SO_3$ or chlorosulfonic acid (CSA) and subsequent neutralization. Ether sulfates suitable for the purposes of the invention correspond to formula (I):

$$R^1O\text{---}(CH_2CH_2O)_m SO_3X \qquad (I)$$

in which $R^1$ is a linear or branched alkyl and/or alkenyl group containing 6 to 22 carbon atoms, m is a number of 1 to 10 and X is an alkali metal and/or alkaline earth metal, ammonium, alkylammonium, alkanolammonium or glucammonium. Typical examples are the sulfates of addition products of on average 1 to 10 and, more particularly, 2 to 5 moles of ethylene oxide with caproic alcohol, caprylic alcohol, 2-ethyl hexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof in the form of their sodium and/or magnesium salts. The ether sulfates may have both a conventional homolog distribution and a narrow homolog distribution. It is particularly preferred to use ether sulfates based on adducts of, on average, 2 to 3 moles of ethylene oxide with technical $C_{12/14}$ or $C_{12/18}$ cocofatty alcohol fractions in the form of their sodium and/or magnesium salts.

Betaines

Betaines are known surfactants which are mainly produced by carboxyalkylation, preferably carboxymethylation, of aminic compounds. The starting materials are preferably condensed with halocarboxylic acids or salts thereof, more particularly with sodium chloroacetate, 1 mole of salt being formed per mole of betaine. The addition of unsaturated carboxylic acids, for example acrylic acid, is also possible. Particulars of the nomenclature and, in particular, the distinction between betaines and "genuine" amphoteric surfactants can be found in the article by U. Ploog in Seifen-Öle-Fette-Wachse, 198, 373 (1982). Other reviews of this subject have been published, for example, by A. O'Lenick et al. in HAPPI, Nov. 70 (1986), by S. Holzman et al. in Tens. Surf. Det. 23, 309 (1986), by R. Bibo et al. in Soap Cosm. Chem. Spec., Apr. 46 (1990) and by P. Ellis et al. in Euro Cosm. 1, 14 (1994). Examples of suitable betaines are the carboxyalkylation products of secondary and, in particular, tertiary amines corresponding to formula (II):

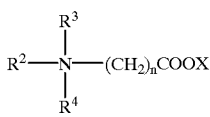

(II)

in which $R^2$ stands for alkyl and/or alkenyl groups containing 6 to 22 carbon atoms, $R^3$ stands for hydrogen or alkyl groups containing 1 to 4 carbon atoms, $R^4$ stands for alkyl groups containing 1 to 4 carbon atoms, n is a number of 1 to 6 and X is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof.

Other suitable betaines are carboxyalkylation products of amido-amines corresponding to formula (III):

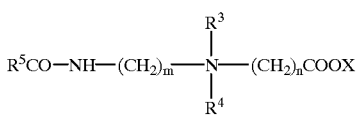

(III)

in which $R^5CO$ is an aliphatic acyl group containing 6 to 22 carbon atoms and 0 or 1 to 3 double bonds, m is a number of 1 to 3 and $R^3$, $R^4$, n and X are as defined above. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethyl aminoethyl amine, N,N-dimethyl aminopropyl amine, N,N-diethyl aminoethyl amine and N,N-diethyl aminopropyl amine which are condensed with sodium chloroacetate. It is preferred to use a condensation product of $C_{8/18}$ cocofatty acid-N,N-dimethyl aminopropyl amide with sodium chloroacetate.

Other suitable starting materials for the betaines to be used in accordance with the invention are imidazolinium betaines. Imidazolinium betaines are also known compounds which may be obtained, for example, by cyclizing condensation of 1 or 2 moles of fatty acid with polyfunctional amines, for example aminoethyl ethanolamine (AEEA) or diethylene triamine. The corresponding carboxyalkylation products are mixtures of different open-chain betaines. Typical examples are condensation products of the above-mentioned fatty acids with AEEA, preferably imidazolines based on lauric acid or—again—$C_{12/14}$ cocofatty acid which are subsequently betainized with sodium chloroacetate.

Alkyl and/or alkenyl oligoglycosides

Alkyl and alkenyl oligoglycosides are known nonionic surfactants which correspond to formula (IV):

(IV)

where $R^6$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90103977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (IV) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl group $R^6$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl group $R^6$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

(Oligo)ethylene glycol fatty acid esters

Ethylene glycol or oligoethylene glycol fatty acid esters suitable as pearlescing waxes correspond to formula (V):

(V)

in which $R^7CO$ is a linear acyl group containing 6 to 22 carbon atoms, X is hydrogen or an acyl group $R^7CO$ and z is a number of 1 to 10 and preferably 1 to 3. Typical examples are ethylene glycol monolaurate, ethylene glycol dilaurate, ethylene glycol monopalmitate, ethylene glycol dipalmitate, ethylene glycol monostearate, ethylene glycol distearate, diethylene glycol monostearate, diethylene glycol distearate and technical mixtures thereof and preferably triethylene glycol mono- and/or distearate. If desired, the esters may be mixed with other known pearlescing waxes, preferably fatty acid alkanolamides, the ratio by weight which is not critical being in the range from 90:10 to 10:50 and preferably in the range from 40:60 to 60:40.

Pearlescing concentrates

According to the invention, particularly preferred pearlescing concentrates have the following general composition:

(a) 20 to 80, preferably 30 to 70% by weight alkyl ether sulfates, (b1) 1 to 30, preferably 5 to 20% by weight betaines and/or (b2) 5 to 30, preferably 5 to 20% by weight alkyl and/or alkenyl oligoglycosides and (c) 1 to 10, preferably 2 to 8% by weight (oligo)ethylene glycol mono- and/or difatty acid esters, with the proviso that the quantities shown add up to 100% by weight, optionally with water and electrolyte salts. In a preferred embodiment, components (a) and (b) are used in a ratio by weight of 5:1 to 20:1, components (a) and (c) are used in a ratio by weight of 5:1 to 30:1 and components (b) and (c) are used in a ratio by weight of 1:1 to 10:1. In one particular embodiment, the ratio by weight of components (a):(b):(c) is (15 to 25):(2 to 4):(0.5 to 2). The pearlescing concentrates normally contain 10 to 70, preferably 30 to 60 and more preferably 40 to 50% by weight of water and optionally 1 to 6 and preferably 2 to 5% by weight of electrolyte salts such as, for example, sodium chloride or magnesium chloride to adjust viscosity.

Commercial Applications

The present invention relates to the use of the aqueous pearlescing concentrates for the production of pearlescent surface-active compositions such as, for example, hair shampoos or manual dishwashing detergents.

The final compositions may contain the pearlescing concentrates according to the invention in quantities of 0.1 to 30 and preferably 1 to 15% by weight, based on the solid content of the concentrates. The compositions, for example hair shampoos, hair lotions, foam baths, cremes or lotions, may additionally contain co-surfactants, oils, co-emulsifiers, superfatting agents, stabilizers, waxes, consistency promoters, thickeners, cationic polymers, silicone compounds, biogenic agents, antidandruff agents, film formers, preservatives, hydrotropes, solubilizers, UV filters, dyes and fragrances as further auxiliaries and additives.

Typical examples of co-surfactants are monoglyceride sulfates, mono- and/or dialkyl sulfosuccinates, fatty acid isethionates, fatty acid sarcosinates, fatty acid taurides, fatty acid taurides, ether carboxylic acids, fatty acid glucamides and/or protein fatty acid condensates.

Suitable oils are, for example, Guerbet alcohols based on $C_{6-18}$ and preferably $C_{8-10}$ fatty alcohols, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer triol) and/or Guerbet alcohols, triglycerides based on $C_{6-10}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, Guerbet carbonates, dialkyl ethers and/or aliphatic or naphthenic hydrocarbons and silicone oils.

Suitable co-emulsifiers are, for example, nonionic surfactants from at least one of the following groups:

(b1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(b2) $C_{12/18}$ fatty acid monoesters and diesters of adducts of 1 to 30 moles of ethylene oxide with glycerol;

(b3) glycerol monoesters and diesters and sorbitan monoesters and diesters of saturated and unsaturated fatty acids containing 6 to 22 carbon atoms and ethylene oxide adducts thereof;

(b4) adducts of 15 to 60 moles of ethylene oxide with castor oil and/or hydrogenated castor oil;

(b5) polyol esters and, in particular, polyglycerol esters such as, for example, polyglycerol polyricinoleate or polyglycerol poly-12-hydroxystearate. Mixtures of compounds from several of these classes are also suitable;

(b6) adducts of 2 to 15 moles of ethylene oxide with castor oil and/or hydrogenated castor oil;

(b7) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b8) trialkyl phosphates;

(b9) wool wax alcohols;

(b10) polysiloxane/polyalkyl polyether copolymers and corresponding derivatives;

(b11) mixed esters of pentaerythritol, fatty acids, citric acid and fatty alcohol according to DE-PS 11 65 574 and/or mixed esters of $C_{6-22}$ fatty acids, methyl glucoside and polyols, preferably glycerol, and (b12) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. The consistency promoters mainly used are fatty alcohols containing 12 to 22 and preferably 16 to 18 carbon atoms and partial glycerides. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines (Polymer J 400, Union Carbide), quaternized collagen polypeptides such as, for example, Lauryldimonium Hydroxypropyl Hydrolyzed Collagen (Lamequat®L, Grünau GmbH), quaternized wheat polypeptides, polyethyleneimine, cationic silicone polymers such as, for example, Amidomethicone or Dow Corning, Dow Corning Co., USA, copolymers of adipic acid and dimethylaminohydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example, bis-dimethylamino-1,3-propane, cationic guar gum such as, for example, Jaguar® CBS, Jaguar® C-17, Jaguar® C-16 of Celanese, USA, quaternized ammonium salt polymers such as, for example, Mirapol® A-15, Mirapol® AD-1, Mirapol® AZ-1 of Miranol, USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, paraffin wax or microwaxes, optionally in combination with hydrophilic waxes, for example cetyl stearyl alcohol. Suitable pearlescent waxes are, in particular, mono- and difatty acid esters of polyalkylene glycols, partial glycerides and esters of fatty alcohols with polybasic carboxylic acids or hydroxycarboxylic acids. Metal salts of fatty acids such as, for example, magnesium, aluminium and/or zinc stearate may be used as stabilizers. In the context of the invention, biogenic agents are, for example, bisabolol, allantoin, phytantriol, panthenol, AHA acids, plant extracts and vitamin complexes. Climbazol, octopirox and zinc pyrithione may be used as antidandruff agents. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. In addition, hydrotropes such as, for example, ethanol, isopropyl alcohol, propylene glycol or glucose may be used to improve flow behavior. Suitable preservatives are, for example, phenoxyethanol, formaldehyde solution, parabens, pentanediol or sorbic acid. The dyes used may be selected from any of the substances which are approved and suitable for cosmetic purposes, as listed for example in the publication "Kosmetische Färbe-mittel" of the Farbstoffkommission der Deutschen Forschungs-gemeinschaft, published by Verlag Chemie, Weinheim, 1984, pages 81–106. These dyes are typically used in concentrations of 0.001 to 0.1% by weight, based on the mixture as a whole.

The total content of auxiliaries and additives may be from 1 to 50% by weight and is preferably from 5 to 40% by weight, based on the composition. The compositions may be produced by standard cold or hot processes and are preferably produced by the phase inversion temperature method.

EXAMPLES

To prepare formulations F1 to F6, the aqueous surface-active emulsifiers were introduced first and heated to 65° C., after which the pearlescing waxes were stirred in. Flowability was then evaluated at 20° C. The symbol "+" stands for flowable, the symbol "−" for non-flowable. The results are set out in Table 1. Formulations F1 to F4 correspond to the invention, formulations F5 and F6 are intended for comparison.

TABLE 1

| Pearlescing concentrates (quantities as % by weight) | | | | | | |
|---|---|---|---|---|---|---|
| INCI Name | F1 | F2 | F3 | F4 | F5 | F6 |
| Sodium Laureth-2 Sulfate | 56 | 50 | 56 | 56 | – | – |
| Sodium Laurylsulfate | – | – | – | – | 56 | 56 |
| Cocoamidopropyl Betaine | 20 | 25 | 15 | – | 20 | 20 |
| Lauryl Polyglucose | – | – | – | 15 | – | – |
| Triethylenglycol Distearate | 2 | – | 2 | 2 | 5 | 4 |
| Monoethylenglycol Distearate | – | 4 | – | – | – | – |
| Cocamide DEA | – | – | 2 | 2 | – | – |
| Sodium chloride | 4 | 4 | 4 | 4 | 4 | – |
| Glycerol | – | – | – | – | – | 15 |
| Water | | | to 100 | | | |
| Stability | + | + | + | + | + | + |

What is claimed is:

1. A pearlescent concentrate comprising:
   (a) from 30 to 80% by weight of an alkyl ether sulfate corresponding to formula I:

$$R^1O-(CH_2CH_2O)_mSO_3X \qquad (I)$$

wherein $R^1$ is a linear or branched alkyl and/or alkenyl group containing from 6 to 22 carbon atoms, m is a number from 1 to 10, and X is a compound selected from the group consisting of an alkali metal, an alkaline earth metal, ammonium, alkylammonium, alkanolammonium, glucammonium, and mixtures thereof;
   (b) from 5 to 20% by weight of a surfactant selected from the group consisting of a betaine corresponding to formula (II):

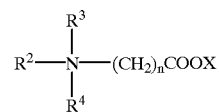

(II)

wherein $R^2$ is an alkyl and/or alkenyl group having from 6 to 22 carbon atoms, $R^3$ is hydrogen or an alkyl group containing from 1 to 4 carbon atoms, $R^4$ is an alkyl group containing from 1 to 4 carbon atoms, n is a number from from 1 to 6 and X is a compound selected from the group consisting of an alkali metal, an alkaline earth metal, ammonium, and mixtures thereof, a betaine corresponding to formula (III):

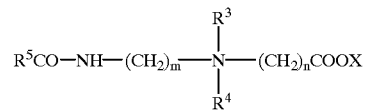

(III)

wherein $R^5CO$ is an aliphatic acyl group having from 6 to 22 carbon atoms and up to 3 double bonds, m is a number from 1 to 3, $R^3$ is hydrogen or an alkyl group containing from 1 to 4 carbon atoms, $R^4$ is an alkyl group containing from 1 to 4 carbon atoms, n is a number from 1 to 6 and X is an alkali metal, an alkaline earth metal or ammonium, an alkyl and/or alkenyl oligoglycoside corresponding to formula (IV):

$$R^6O-[G]_p \qquad (IV)$$

wherein $R^6$ is an alkyl and/or alkenyl group containing from 4 to 22 carbon atoms, G is a sugar unit containing 5 or 6 carbon atoms and p is a number from 1 to 10, and mixtures thereof; and (c) from 1 to 10% by weight of an (oligo)ethylene glycol mono- and/or difatty acid ester, all weights being based on the total weight of the composition, and wherein the concentrate is polyol-free.

2. The concentrate of claim 1 wherein the surfactant is the betaine corresponding to formula (II).

3. The concentrate of claim 1 wherein the surfactant is the betaine corresponding to formula (III).

4. The concentrate of claim 1 wherein the surfactant is the alkyl and/or alkenyl oligoglycoside corresponding to formula (IV).

5. The concentrate of claim 1 wherein the alkyl ether sulfate is present in the composition in an amount of from 30 to 70% by weight, based on the weight of the composition.

6. The concentrate of claim 1 wherein water is present in the composition in an amount of from 10 to 70% by weight, based on the weight of the composition.

7. The concentrate of claim 1 further containing from 1 to 6% by weight, based on the weight of the composition, of an electrolyte salt.

8. A pearlescent surface-active composition containing from 0.1 to 30% by weight, based on the weight of the composition, of the concentrate of claim 1.

9. A process for imparting pearlescence to a surface-active composition comprising adding an effective amount of a pearlescent concentrate to the composition, the pearlescent concentrate comprising:

(a) from 30 to 80% by weight of an alkyl ether sulfate corresponding to formula I:

wherein $R^1$ is a linear or branched alkyl and/or alkenyl group containing from 6 to 22 carbon atoms, m is a number from 1 to 10, and X is a compound selected from the group consisting of an alkali metal, an alkaline earth metal, ammonium, alkylammonium, alkanolammonium, glucammonium, and mixtures thereof;

(b) from 5 to 20% by weight of a surfactant selected from the group consisting of a betaine corresponding to formula (II):

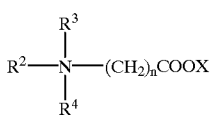

wherein $R^2$ is an alkyl and/or alkenyl group having from 6 to 22 carbon atoms, $R^3$ is hydrogen or an alkyl group containing from 1 to 4 carbon atoms, $R^4$ is an alkyl group containing from 1 to 4 carbon atoms, n is a number from 1 to 6 and X is a compound selected from the group consisting of an alkali metal, an alkaline earth metal, ammonium, and mixtures thereof, a betaine corresponding to formula (III):

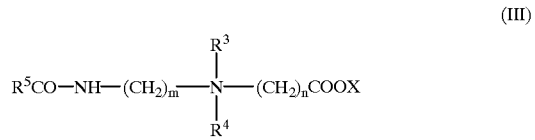

wherein $R^5CO$ is an aliphatic acyl group having from 6 to 22 carbon atoms and up to 3 double bonds, m is a number from 1 to 3, $R^3$ is hydrogen or an alkyl group containing from 1 to 4 carbon atoms, $R^4$ is an alkyl group containing from 1 to 4 carbon atoms, n is a number from 1 to 6 and X is an alkali metal, an alkaline earth metal or ammonium, an alkyl and/or alkenyl oligoglycoside corresponding to formula (IV):

wherein $R^6$ is an alkyl and/or alkenyl group containing from 4 to 22 carbon atoms, G is a sugar unit containing 5 or 6 carbon atoms and p is a number from 1 to 10, and mixtures thereof; and (c) from 1 to 10% by weight of an (oligo)ethylene glycol mono- and/or difatty acid ester, all weights being based on the total weight of the composition, and wherein the concentrate is polyol-free.

10. The process of claim 9 wherein the surfactant is the betaine corresponding to formula (II).

11. The process of claim 9 wherein the surfactant is the betaine corresponding to formula (III).

12. The process of claim 9 wherein the surfactant is the alkyl and/or alkenyl oligoglycoside corresponding to formula (IV).

13. The process of claim 9 wherein the alkyl ether sulfate is present in the composition in an amount of from 30 to 70% by weight, based on the weight of the composition.

14. The process of claim 9 wherein water is present in the composition in an amount of from 10 to 70% by weight, based on the weight of the composition.

15. The process of claim 9 wherein the concentrate further contains from 1 to 6% by weight, based on the weight of the composition, of an electrolyte salt.

16. The process of claim 9 wherein the pearlescent concentrate is added to the surface-active composition in an amount of from 0.1 to 30% by weight, based on the weight of the composition.

* * * * *